United States Patent
Voit et al.

(10) Patent No.: US 9,739,704 B2
(45) Date of Patent: Aug. 22, 2017

(54) FLUID PROCESSING TUBE CAPABLE OF BEING USED IN OPTICAL ANALYSIS AND METHOD FOR OPTICALLY ANALYZING A FLUID

(75) Inventors: Thomas Voit, Hilden (DE); Michael Geissler, Cologne (DE); Harald Quintel, Steckborn (CH); Roman Gruler, Rottweil (DE)

(73) Assignee: QIAGEN GMBH, Hilden (DE)

( * ) Notice: Subject to any disclaimer, the term of this patent is extended or adjusted under 35 U.S.C. 154(b) by 36 days.

(21) Appl. No.: 13/990,692

(22) PCT Filed: Nov. 23, 2011

(86) PCT No.: PCT/EP2011/070807
§ 371 (c)(1),
(2), (4) Date: Aug. 14, 2013

(87) PCT Pub. No.: WO2012/076337
PCT Pub. Date: Jun. 14, 2012

(65) Prior Publication Data
US 2013/0314697 A1    Nov. 28, 2013

(30) Foreign Application Priority Data

Dec. 8, 2010 (EP) .................................... 10194183

(51) Int. Cl.
*G01N 21/03* (2006.01)
*B01L 3/00* (2006.01)
*G01N 21/64* (2006.01)

(52) U.S. Cl.
CPC .......... *G01N 21/03* (2013.01); *B01L 3/50825* (2013.01); *G01N 21/0303* (2013.01);
(Continued)

(58) Field of Classification Search
CPC ............. G01N 21/0303; G01N 21/031; G01N 2021/0389; G01N 2021/0392;
(Continued)

(56) References Cited

U.S. PATENT DOCUMENTS 3,964,867 A * 6/1976 Berry ................... G01N 21/253
356/246
4,021,124 A * 5/1977 Sarstedt ................. G01N 21/03
250/576

(Continued)

FOREIGN PATENT DOCUMENTS

WO    2008003182 A1    1/2008
WO    2008004695 A1    1/2008

OTHER PUBLICATIONS

International Search Report for PCT/EP2011/070807 Mailed Jan. 9, 2012.

*Primary Examiner* — Michael P Lapage
(74) *Attorney, Agent, or Firm* — McBee Moore Woodward & Vanik IP, LLC; Susan McBee (57) ABSTRACT

Fluid processing tube for use in optical analysis comprising at least one first portion being made from a first material suitable for optical analysis and being configured to include two optical paths of different lengths, and at least one second portion connected to said first portion and being made from a second material different from said first material.

24 Claims, 7 Drawing Sheets

(52) U.S. Cl.
CPC ... *B01L 2300/043* (2013.01); *B01L 2300/047* (2013.01); *B01L 2300/0654* (2013.01); *G01N 2021/0378* (2013.01); *G01N 2021/6482* (2013.01); *G01N 2201/066* (2013.01)

(58) Field of Classification Search
CPC ..... G01N 2021/0378; G01N 2021/036; G01N 2021/0382; G01N 21/03–2021/0396; B01L 3/50825; B01L 2300/043; B01L 2300/047; B01L 2300/0654
See application file for complete search history.

(56) References Cited

U.S. PATENT DOCUMENTS

| | | | |
|---|---|---|---|
| 4,029,958 A * | 6/1977 | Wright | 250/223 B |
| 4,283,141 A * | 8/1981 | Stockdale | B01F 11/0082 356/246 |
| 6,221,655 B1 * | 4/2001 | Fung | B01L 3/5021 422/504 |
| 2003/0152492 A1* | 8/2003 | Chang et al. | 422/99 |
| 2006/0068459 A1 | 3/2006 | Jay | |
| 2007/0081159 A1 | 4/2007 | Giffin et al. | |
| 2007/0128080 A1 | 6/2007 | Lohn | |
| 2007/0272689 A1* | 11/2007 | Mitsuhashi | A61B 10/0096 220/200 |
| 2008/0123091 A1 | 5/2008 | Yamamoto et al. | |
| 2010/0007888 A1* | 1/2010 | Glover | 356/436 |
| 2012/0029832 A1* | 2/2012 | Dodgson | B01L 3/50825 702/19 |

* cited by examiner

FLUID PROCESSING TUBE CAPABLE OF BEING USED IN OPTICAL ANALYSIS AND METHOD FOR OPTICALLY ANALYZING A FLUID

CROSS REFERENCE TO RELATED APPLICATIONS

This application is a §371 National Stage Application of PCT/EP2011/070807, filed Nov. 23, 2011, which claims priority to European Application No. 10194183.9, filed Dec. 8, 2010.

BACKGROUND OF THE INVENTION

Field of the Invention

The present invention relates to a fluid processing tube or storage container and a method for analyzing a fluid. More specifically, the present invention relates to a tube and a method for in-line quantification of including but not limited to DNA, RNA, salts and proteins by optical analysis techniques. In particular, the present invention relates to quantification of including but not limited to DNA, RNA, safe and proteins by measuring optical transmittance.

Description of Related Art

In many technical fields like chemistry, biology, medicine or environmental protection, fluids have to be analysed before, during or after being stored, processed or brought into reaction with each other. For this purpose, fluids are centrifuged, stored, mixed, filtered, cooled, heated, decomposed, washed, pipetted, or treated by other procedures. In order to prepare and analyze a fluid, often a long sequence of analyzing and processing steps, which may be iterative, is necessary. In many cases, large sets of different fluids need to be processed and analyzed according to the same procedure. Sometimes, sequences or batches of the same fluid need to be processed and analyzed in parallel.

Optical analysis procedures are known in the art and frequently used to analyze fluids. Optical analysis may include measuring transmittance, fluorescence, chemoluminescence, bioluminescence and fluorescence resonance energy transfer (FRET). In many cases, a fluid is optically analyzed by measuring optical transmittance. Transmittance is the fraction of incident light of a beam at a specified wavelength that passes through a sample. The term "light" according to the present invention refers to electromagnetic radiation of any wavelength, in particular, the term light refers to electromagnetic radiation in the wavelengths of ultraviolet and visible light. Most preferably, the term light refers to electromagnetic radiation in the wavelengths of about 220 to about 400 nm (ultraviolet light). By measuring the intensity of the light coming out of the sample, absorbance and optical density of a fluid at a certain wavelength or many different wave-lengths can be assessed.

In a fluid, according to Beer-Lambert's law, absorption is linearly dependent on the length of the optical path, the molar extinction coefficient of the absorbing chemical species and the concentration of the chemical species in the fluid. The length of the optical path is the distance that the lightbeam travels in the fluid. Thus, for example, when the length of the optical path and the molar extinction coefficient of a chemical species are known, the concentration of the species in the fluid can be assessed. For quantifying salts, DNA, RNA and proteins and assessing their concentrations within a fluid, it is desirable to measure optical transmittance at the wavelengths of about 230 nm (salts), of about 280 nm (DNA and RNA) and of about 280 nm (proteins). In order to quantify all compounds in a single measurement, it is particularly desirable to measure optical transmittance over the entire range of about 220 to about 400 nm.

Generally, a container for containing a fluid is used in optical analysis. The side-wall of such a container comprises at least one area which does not absorb, refract or reflect light in the wavelengths of interest for the optical analysis procedure or only absorbs, refracts or reflects a small fraction thereof. Cyclic olefin copolymers, cyclic olefin polymers, polymethylpenten, graphene and PTFE are known for showing no or low absorption of light for a wide range of wavelengths.

Apparatuses for measuring transmittance, for example spectrophotometers, generally allow assessing absorption exactly in a specified range of absorptions. As absorption is linearly dependent on the length of the optical path and the concentration of the chemical species, measuring absorption for optical paths of different lengths is frequently desirable, in order to assess a wide range of concentrations of different chemical species. To minimize the lightbeam from being refracted or reflected, the side-wall of the container containing the fluid should be perpendicular to the lightbeam at the points where the beam passes through the side-wall.

Small volumes of fluids are often processed and stored in microcentrifuge tubes commonly known as Eppendorf tubes. Microcentrifuge tubes are small, cylindrical plastic containers, typically having conical bottoms and a closable cap. They are frequently made from polypropylene and considered to be disposable.

However, commonly used microcentrifuge tubes are not suitable for optical analysis, because they are not transparent enough in the desired wavelengths. Reasons for this may be, inter alia, the polymers used being crystalline or partly crystalline, the polymeric materials absorbing light in the same wavelengths as the chemical species or the configuration of the tube side-wall leading to reflection and/or refraction of the light beam. In particular, the material used for microcentrifuge tubes absorbs light in the wavelengths of 220 to 240 nm and is partly crystalline. Thus, microcentrifuge tubes do not allow quantification of DNA, RNA, salts and proteins. Furthermore, microcentrifuge tubes do not provide optical paths of different, predefined lengths.

Thus, fluids processed in commonly used microcentrifuge tubes have to be transferred to other containers for being optically analyzed. Therefore, the microcentrifuge tube has to be opened and the fluid transferred, e.g., pipetted. This may be time consuming, limit the throughput and be prone to errors during the procedure. In particular, when a long sequence of analyzing and processing steps is necessary to prepare and analyze the fluid, large sets of different fluids need to be processed and analyzed according to the same procedure, or sequences or batches of the same fluid need to be processed and analyzed in parallel. Opening or transferring the sample also involves the risk of contamination. Furthermore, opening or transferring the sample involves the risk of sample loss, e.g. by evaporation or because crops remain in the tube or the pipette. When the fluid has to be transferred several times, because the optical path of the container selected is to short or to long, risks of contamination and sample loss are even greater. Having to open the tube and transferring the content also requires additional steps in automated in-line processing and analysis apparatuses.

Furthermore, commonly used microcentrifuge tubes are not suitable for carrying out certain processing, storing, and reaction steps, in particular, commonly used microcentrifuge tubes are not resistant to some regularly used solvents, which may also be used for optical analysis.

Containers for optical analysis can not be used for storing and processing fluids. For example, they can not be suitably closed. One reason for this is that the materials used for the containers are not soft enough to allow configuration of a closable cap. In particular, no containers having a cap attached over a joint to the fluid containing part of the container are known in the art. However, when the cap is not attached to the fluid containing part of the container, this may lead to errors during the procedure and cross contamination, e.g., when caps are accidentally interchanged. Furthermore, loose caps may pose problems for automated in-line processing apparatuses, e.g., because the caps will fall off when opened.

SUMMARY

In order to overcome one or several of the above mentioned problems, and in order to improve known methods of processing fluids, fluid processing tubes according to independent claims 1 and 2 and methods for processing fluids according to independent claim 21 are provided.

Further aspects, improvements and variations are disclosed in the dependent claims, the figures and the descriptions.

With the fluid processing tubes according to claims 1 and 2 and the method according to claim 21, it is possible to carry out a wide range of different processing, storing and analysis procedures involving one or more analysis and processing steps, in particular, it is possible to provide for fully automated and standardised analysis and processing procedures for a variety of fluids, preferably without any manual intervention. These fluids may contain biomolecules. The fluid processing tubes and methods provided by the invention can further be used for fluid analysis and processing without necessity of opening the tubes. Thus, the risk of contamination and sample loss can be minimized. Further, the fluid processing tube can be used as a disposable tube.

Furthermore, with the fluid processing tubes having a cap connected over a joint to the fluid containing part of the tube, the cap can be uniquely assigned to the tube. Thus, cross-contamination and likelihood of confusing the tubes can be minimized. Misallocation of caps in automated in-line processing and optical analysis apparatuses is prevented.

According to a first aspect of the present invention, the fluid processing tube for use in optical analysis comprises at least one first portion being made from a first material suitable for optical analysis and being configured to include two optical paths of different lengths, and at least one second portion connected to said first portion and being made from a second material different from said first material.

According to a further aspect of the present invention, the fluid processing tube for use in optical analysis comprises at least one first portion suitable for optical analysis and being configured to contain a fluid, and at least one second portion connected to said first portion being configured to include a cap for closing the fluid containing part of the tube, wherein the cap is connected to the fluid containing part of the tube over a joint. According to one embodiment of this aspect of the invention the first portion and second portion are made from the same or a similar material. According to another embodiment of this aspect of the invention the first portion is made from a first material suitable for optical analysis and the second portion is made from a second material less brittle than said first material.

BRIEF DESCRIPTION OF THE DRAWINGS

FIGS. 1A-7B represent embodiments as described herein.

DETAILED DESCRIPTION OF A PREFERRED EMBODIMENT

A fluid processing tube according to any aspect of the present invention preferably is suitable for nucleic acid quantification. Preferably, the tube is suitable for in-line quantification of DNA and/or RNA and/or salts and/or proteins. Preferably, the tube is disposable. Preferably, the tube is suitable for storing fluids.

According to any aspect of the present invention, the second portion of the tube may be positioned proximal to the opening of the tube, while the first portion of the tube is positioned distal of the second portion.

Furthermore, the first portion of the fluid processing tube according to any aspect of the present invention may comprise an optical detection zone. The optical detection zone preferably has no weld lines. Preferably, the optical detection zone is positioned at the end of the tube which is opposite the opening. To allow analysis of small volumes, the inner volume of the optical detection zone should be approximately 15 microliter or less. Preferably, the side walls of the optical detection zone comprise planar areas. Preferably, the optical detection zone has a rectangular and/or a polygonal cross-section when viewed in direction of the longitudinal axis of the tube.

According to a further aspect of the present invention, the first portion of the fluid processing tube is configured to include two optical paths of different lengths. Preferably, the length of the longest optical path is at least three times the length of the shortest optical path. This may be realized by the optical detection zone having a polygonal cross-section when viewed in direction of the longitudinal axis of the tube. Preferably, the cross-section is rectangular.

The fluid processing tube according to any aspect of the present invention preferably comprises a fluid containing part. The fluid containing part may comprise a rim. Furthermore, the fluid processing tube according to any aspect of the present invention preferably comprises at least one cap. Preferably, the cap is connected to the fluid containing part of the tube over a joint. The cap and/or the tube may comprise at least one cap fixture means for holding the cap when being closed.

Preferably, the cap is comprised by the second portion of the tube. In some embodiments, the second portion may consist of the at least one cap. In other embodiments the second portion consist of the at least one cap and means for connecting the cap to the fluid containing part of the tube over a joint. In further embodiments the second portion may comprise the cap and a joint for connecting the cap to the fluid containing part of the tube. In some embodiments the second portion may comprise the cap, a joint for connecting the cap to the fluid containing part of the tube and a portion of the fluid containing part of the tube.

The joint between the fluid containing part of the tube and the cap may be a film joint or a form-fitted joint. The joint may be created in in-mold assembly. The joint may also be a snap-connection.

The second portion of the fluid processing tube according to the present invention may be connected to the first portion by any means know in the art. For example, the second portion may be integral with the first portion. Alternatively, the first portion and the second portion may be welded and/or fused and/or bonded and/or form-fitted and/or frictional-fitted and/or solvent-fitted to each other. The first portion and the second portion may also be connected by any combination of these methods.

According to any aspect of the present invention, the first portion and the second portion of the tube may be welded with each other next to the optical detection zone. Alternatively, the first portion and the second portion may be welded near the opening of the tube. In further alternatives, the first portion and the second portion may be fused near the joint between the tube and the cap. When form-fitted, the first portion and the second portion of the tube may be mechanically interlocked or connected by a snap-connection. The snap-connection can be releasable or non-releasable.

According to any aspect of the present invention, the first portion may be connected to the second portion over a third portion. According to some aspects of this invention, the second portion may be connected to the first portion at the joint between the cap and the fluid containing part of the tube.

In any aspect of the present invention, the first material used to make the first portion of the tube preferably should be suitable for optical analysis in the wavelengths of about 230 nm and/or about 260 nm and/or about 280 nm. More preferably, the first material is suitable for optical analysis in the wavelengths of about 220 to 330 nm. Most preferably, the first material is suitable for optical analysis in the wavelengths of about 220 to 400 nm. With regard to the wavelengths, the term "about" relates to ranges around the exactly mentioned values of ±five nm, ±four nm, ±three nm, ±two nm, or ±one nm.

The first material preferably is selected from the group comprising cyclic olefin copolymers, cyclic olefin polymers, polymethylpenten, graphene, PTFE and glass. Most preferably cyclic olefin copolymers or glass are used as the first material, because they have been found to show the best transmittance in the desired ranges. Preferably, cyclic olefin copolymer is Topas® COC 8007X10 (Topas Advanced Polymers GmbH, Frankfurt, Germany). The cyclic olefin polymer preferably is Zeonex® 480 (Zeon Europe GmbH, Düsseldorf, Germany). The polymethylpenten preferably is TPX (Mitsui Chemicals, Tokio, Japan). Graphene preferably is used as a raw material and/or as an additive. The PTFE preferably is Teflon AF (DuPont).

In any aspect of the present invention, the second material being used to make the second portion of the tube preferably is softer and/or less brittle than the first material. The second material preferably is polypropylene or polyethylene.

Preferably, the fluid processing tube according to any aspect of the present invention is configured for being exposed to an acceleration of at least 100 g, more preferably 1000 g and most preferably 10000 g when centrifuged.

According to a further aspect of the present invention, the method for optically analyzing the fluid comprises filling a fluid into a test tube according to the present invention and optically analyzing the fluid in the test tube. The method preferably is used for quantification of nucleic acids. Preferably, DNA and/or RNA and/or salts and/or proteins in a fluid are analyzed with the method in an in-line quantification apparatus.

According to a further aspect of the present invention, use of a fluid processing tube according to the present invention for processing and/or optically analyzing and/or storing a fluid is claimed.

It is one aspect of the present invention to improve methods of processing fluids that use optical analysis. For that purpose, the present invention provides fluid processing tubes for use in optical analysis, processing, reaction, and storage of fluids. The fluid processing tubes according to the invention may be used for measuring optical transmittance, fluorescence, chemoluminescence, bioluminescence, and fluorescence resonance energy transfer (FRET). Preferably, the fluid processing tubes according to the invention are suitable for nucleic acid quantification and can be used for quantification of DNA, RNA, salts and proteins by measuring optical transmittance. More preferably, the tubes also allow in-line analysis of fluids. Preferably, the fluid processing tubes according to the invention are suitable for centrifugation. The tubes are disposable and mechanically resistant.

It is another aspect of the invention to provide a disposable end mechanically resistant tube that can be used for processing fluids with most commonly used solvents. For this purpose, the present invention provides a fluid processing tube wherein the fluid containing part of the tube is at least partly made from a material resistant to a variety of commonly used solvents. In order to allow processing of the fluids, the tube has at least one cap of a second material connected to the fluid containing part of the tube over a joint. Preferably, the tube can be used for optical analysis, in particular measuring optical transmittance, fluorescence, chemoluminescence, bioluminescence, and fluorescence resonance energy transfer (FRET). Preferably, the fluid processing tube is suitable, for nucleic acid quantification. In particular, the tube should be suitable for quantification of DNA, RNA, salts and proteins by measuring optical transmittance and allow in-line analysis of fluids. Preferably, the fluid processing tube according to the invention is suitable for centrifugation.

Preferably, the first portion of the tube is configured to include at least two optical paths of different lengths, in order to allow measuring optical transmittance for a wider range of concentrations of different chemical species. In order to allow measurement of optical transmittance in three orders of magnitude or more, the length of the longest optical path more preferably is at least three times the length of the shortest optical path.

The fluid processing tube according to any aspect of the present invention may comprise at least one fluid containing part for containing a fluid in the container and at least one cap for closing the fluid containing part of the tube such that the fluid contained in the fluid containing part can not leak. The cap may be connected to the fluid containing part of the tube over a joint. Preferably, the cap and/or the fluid containing part of the tube comprise at least one cap fixture means for holding the cap when being closed, in order to prevent the cap from opening accidentally. Additionally, the fluid containing part of a tube according to any aspect of the present invention may comprise a rim.

According to any aspect of the invention, the first portion of the tube may comprise at least one optical detection zone. The optical detection zone is a zone of the first portion of the tube configured for optical analysis of the fluid in the tube. In order to allow analysis of small samples, the optical detection zone preferably is positioned at the lowest pad of the tube during analysis, which in general is the end of the tube opposite the opening. Hence, the tube preferably has the following configuration: the second portion of the tube is proximal to the tube opening, the first portion of the tube is distal of the second portion, and the optical detection zone is positioned at the end of the tube opposite the opening. Thus, the optical detection zone preferably is positioned at the distal end of the tube.

Preferably, the side-wall of the optical detection zone comprises at least one planar area. More preferably, the side wall of the optical detection zone comprises at least two planar areas on opposite sides of the tube through which a light beam can enter and exit the tube perpendicularly. The optical path provided thereby is advantageous, inter alia, for measuring optical transmittance, because reflection of a lightbeam entering and exiting the tuba is minimised. The optical path may be perpendicular to the longitudinal axis of the tube or not. The optical path may intersect the longitudinal axis of the tube or not. To further prevent refraction of the light beam, the at least one planar area of the side-wall of the optical defection zone preferably has no weld lines or any other defects that could cause refraction of the lightbeam. If the side-wall of the optical detection zone comprises at least one planar area, the rest of the side-wall of the fluid containing part of the tube does not have to comprise a planar area. In fact, the rest of the side-wall of the fluid containing part of the tube may have any suitable cross-section and preferably is elliptical, more preferably almost cylindrical, and most preferably cylindrical. The cross-section of the rest of the side-wall of the fluid containing part of the tube may change into a cross-section comprising a planar area gradually or abruptly. Thus, the fluid containing part of the tube may include a transition zone for transition between the different cross-sections. The transition zone may be comprised by the first portion, the second portion or both.

In addition to the first pair, the side-wall of the optical detection zone may comprise at least one second pair of planar areas on opposite sides of the tube. Preferably, the thickness of the side-wall of the optical detection zone in the second pair of planar areas is equal to the thickness of the side-wall of the optical detection zone in the first pair of planar areas, because then the measurements can be easily compared. Preferably, the distance between the inner surfaces of the second pair of planer areas is longer than the distance between the inner surfaces of the first pair of planar areas. This means that the optical path between the second pair of planar areas preferably is longer than the optical path between the first pair of planar areas, in order to allow measurement of optical transmittance in three orders of magnitude or more, the length of the longer optical path preferably is at least three times the length of the shorter optical path. The optical path between the second pair of planar areas and the first pair of planar areas may be in the same plane or in different planes. The optical paths may be offset along the longitudinal axis or not, intersect the longitudinal axis or not, intersect each other or not, or may be parallel or not.

Preferably, different optical paths are provided for different angles of rotation along the longitudinal axis of the tube. This may be achieved by configuring all planar areas of the pairs of planar areas of the side-wall of the optical detection zone parallel to the longitudinal axis of the tube. In this case, the optical detection zone may have a polygonal cross-section when viewed in direction of the longitudinal axis of the tube. Preferably, the optical detection zone has a rectangular cross-section when viewed in direction of the longitudinal axis of the tube. Then, two optical paths of different lengths will be provided in the first portion of the tube. The optical paths will be perpendicular to each other and perpendicular to the longitudinal axis of the tube. The rest of the side-wall of the fluid containing part of the tube may have any suitable cross-section and preferably is elliptical, more preferably almost cylindrical, and most preferably cylindrical. The cross-section of the rest of the side-wall of the fluid containing part of the tube may change into the polygonal or rectangular cross-section of the side-wall in the optical detection zone gradually or abruptly. Thus, the fluid containing part of the tube may include a transition zone for transition between the different cross-sections. The transition zone may be comprised by the first portion, the second portion, or both.

When a fluid processing tube according to any aspect of the present invention comprises at least one cap, the cap preferably is comprised by the second portion of the tube. Depending on the specific embodiment of the invention, the second portion may consist of the cap, the cap and means for connecting the cap to the fluid containing part of the tube over a joint, the cap and the joint, or comprise the cap, the joint and a portion of the fluid containing part of the tube. The joint between the fluid containing part of the tube and the cap may be a film joint or a form-fitted joint. The form-fitted joint may be created in in-mold assembly or configured as a snap-connection.

The second portion of a fluid processing tube according to any aspect of the present invention may be connected to the first portion by any suitable method. Methods may include but are not limited to welding, fusing, bonding, form-fitting, frictional fitting and solvent-fitting. Fusing or welding may include but is not limited to frictional welding, ultrasonic welding and high frequency welding. Furthermore, combinations of those methods are contemplated. For example, the first and second portion of the tube may be form-fitted or frictional fitted end subsequently bonded, fused or welded. Alternatively, the first and second portion of a fluid processing tube according to any aspect of the present invention may also be formed integrally.

Different forms of welding or fusing the first and second portion of the lube are contemplated. For example, the first and second portion may be welded next to the optical detection zone. Nevertheless, the first and second portion of the tube can also be fused or welded near the opening of the tube. Fusing or welding the first and second portions near the opening of the tube seems advantageous, because in this case most of the fluid containing part of the tube is made from the first material, which may be a material more resistant to commonly used solvents. Fusing or welding the first and second portion of the tube near the joint between the tube and the cap is considered as a further alternative. For example, when the lube comprises a rim, the first and second portion of the tube may be fused or welded at the rim of the tube.

A form-fitted connection between the first and second portion of the tube may be realized by any technique known in the art. For example, the tubes may be mechanically interlocked if a suitable geometry or suitable locking means are provided on the outer and/or inner surface of the first and/or second portion. Additionally the tube may be sealed by bonding, welding and/or fusing the portions. Furthermore, the first and second portion can be form-fitted by a snap connection, which may be configured to be releasable or non-releasable if the snap-connection is releasable, the second portion may be easily detachable from the first portion. When the snap-connection is non-releasable, detaching the second portion from the first portion is not be possible without damaging one of the portions.

The first and second portion of the tube may also be connected at the joint between the fluid containing part of the tube and the cap. For example, the joint can be a formatted joint, wherein part of the joint is comprised by the first portion and part of the joint is comprised by the second portion of the tube. Form-fitted joints may be created in in-mold assembly during injection molding or as snap-connections.

Connecting the first portion to the second portion over at least one third portion is also contemplated. In this case, any of the techniques described above or combinations thereof may be used for connecting each of the portions.

Fluid processing tubes according to any aspect of the present invention comprise at least one first portion being made from a first material suitable for optical analysis and at least one second portion connected to said first portion and being made from a second material said first material. Preferably, the first material is suitable for optical analysis at the wavelength of about 230 nm to allow quantification of salts and/or of a about 260 nm to allow quantification of DMA and RNA and/or of about 280 nm to allow quantification of proteins. More preferably the first material is suitable for optical analysis in the ranges of about 220 to about 250 nm and/or of about 250 to about 270 nm and/or of about 270 to about 290 nm. Even more preferably, the first material is suitable for optical analysis in the wavelengths of about 220 to about 380 nm. Most preferably, the first material is suitable for optical analysis in the wavelengths of about 220 to about 400 nm. A material is suitable for optical analysis at a certain wavelength or over a range of wavelengths, if it does not absorb, refract or reflect light in these wavelengths or only absorbs, refracts or reflects a small fraction thereof. In particular, the material has to be highly amorphous, because crystals may cause refraction of the lightbeam. Furthermore, the first material of any embodiment of the present invention preferably is resistant to commonly used solvents and does not absorb moisture.

Highly amorphous materials suitable for optical analysis at all or at least some of these wavelengths are cyclic olefin copolymers, cyclic olefin polymers, polymethylpenten, graphene, polytetrafluoroethylene (PTFE) and glass. Furthermore, some of these materials are resistant to commonly used solvents and show low moisture absorption. For example, cyclic olefin copolymers may be resistant to Acetone, Butanone and polar solvents. The first material of a tube according to the present invention therefore preferably is a material selected from the group consisting of cyclic olefin copolymers, cyclic olefin polymers, polymethylpenten, graphene and PTFE. More specifically, the cyclic olefin copolymer may be Topas® COC 8007X10 (Topas Advanced Polymers GmbH, Frankfurt, Germany), the cyclic olefin polymer may be Zeonex® 480 (Zeon Europe GmbH, Düsseldorf, Germany), the polymethylpenten may be TPX (Mitsui Chemicals, Tokio, Japan) and Teflon AF (DuPont, Wilmington, USA) may be used as PTFE. Graphene may be used as a raw material or as an additive. Because transmittance suitable for optical measurements over some or most or all of the desired wavelengths has been assessed, the first material most preferably is selected from the group consisting of cyclic olefin copolymers and glasses.

Because highly amorphous materials are very brittle, cap holding means for holding a cap on the fluid containing part of the tube when the cap is closed can not be suitably configured from them. This problem is solved by fluid processing tubes according to the present invention comprising a second portion connected to the first portion and being made from a second material different from the first material. Furthermore, because highly amorphous materials are very brittle, joints resisting many movements can not be suitably configured. This problem is solved by fluid processing tubes according to some embodiments of the present invention in which the cap is connected to the fluid containing part of the tube over a joint and at least a part of the joint being made from a second material different from the first material. For implementing these advantages optimally, the second material should be less brittle than the first material. Preferably, the second material is also softer than the first material. For example, polypropylene or polyethylene could be used as the second material.

Any tube according to the present invention preferably is configured for being connected to the rotor of a centrifuge. Preferably, any tube according to the present invention is configured for centrifugation on standard centrifuges. By having the centrifuge rotate the rotor, a centrifugal force can be applied to the fluid processing tube. For example, the tubes should be configured for being exposed to an acceleration of at least 100 g or preferably at least 1000 g or most preferably at least 10000 g when centrifuged. The tube may be connected to the rotor by any means suitable therefore. Preferably, the tube has a rim configured to hold the tube in position when the rotor is rotated.

The tube according to any embodiment of the present invention preferably allows for the optical analysis of volumes as little as 15 microliter. Therefore, the inner volume of the optical detection zone preferably is approximately 15 microliter or less.

A further aspect of the present invention is a method including the step of filling a fluid into a lube according to the present invention, processing the fluid in the tube and optically analyzing the fluid in the tube. One or all of the steps of the method may be performed automatically. Furthermore, optical analysis may comprise measuring optical transmittance for quantifying DNA and/or RNA and/or salts and/or proteins contained in the fluid.

Fluid processing tubes and fluid processing methods according to the claims allow to carry out a wide range of different processing, reaction, analysis, and storing procedures involving one or more tubes or other disposable articles (e.g. spin columns, collection tubes, etc) within one and the same fluid processing tube, in particular, it is possible to provide fully automated and standardized processing and optical analysis for a variety of proteins, salts, DNA, RNA and in a single fluid processing tube. This minimizes the time consumed for processing and analysis, in particular when a long sequence of analyzing and processing steps is necessary, large sets of different fluids need to be processed and analysed according to the same procedure or sequences or batches of the same fluid need to be processed and analyzed in parallel. At the same time, risk of contamination, cross-contamination and sample loss, inter alia, can be minimized. The processes can be automated more easily and tube can be used as a disposable article.

The following Figures below disclose several embodiments according to the invention for illustrational purposes only. In particular, the disclosure within the Figures is not meant to limit the range of protection of the invention:

Figures 1A, 1B:
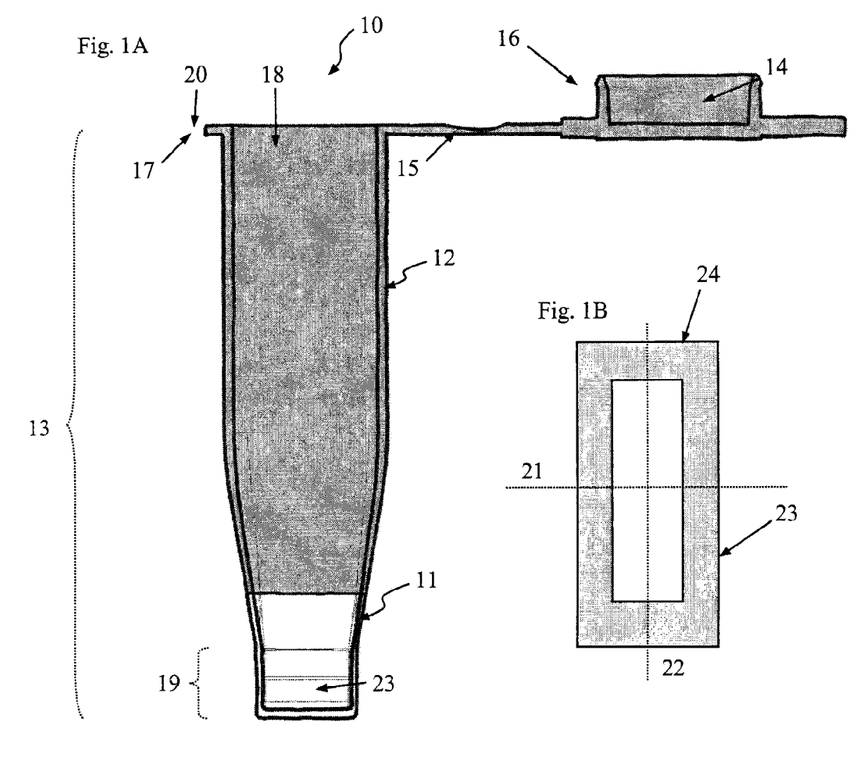
FIG. 1A-1B: Fluid processing tube according to the invention comprising a first portion and a second portion.

FIG. 1A discloses a first example of a tube 10 for use in optical analysis. The tube 10 consists of a first portion 11 and a second portion 12. The first portion 11 is made from a first material suitable for optical analysis. The second portion 12 is made from a second material different from said first material. The second portion 12 of tube 10 may be connected to the first portion 11 by any technique known in the art. As shown in FIG. 1A the second portion may be integrally connected, bonded or welded to the first portion 11.

The fluid containing part 13 of tube 10 in FIG. 1A is formed by first portion 11 and second portion 12. Second portion 12 comprises cap 14 connected to the fluid containing part 13 of tube 10 over joint 15. For tube 10 shown in FIG. 1 joint 15 is a film joint. Cap 14 comprises cap closing means 15 for holding cap 14 on fluid containing part 13 of tube 10 when cap 14 is closed. Fluid containing part 13 of tube 10 in FIG. 1A also comprises means 17 for connecting tube 10 to the rotor of a centrifuge (not shown). Means 17 can be rim 20.

At the end of tube 10 opposite opening 18, first portion 11 of tube 10 comprises optical detection zone 19. As shown in FIG. 1B, optical detection zone 19 has a rectangular cross-section when viewed in direction of the longitudinal axis of the tube. Optical detection zone 19 comprises two pairs of planar side-walls 23 and 24 on opposite sides of tube 10 and two optical paths 21 and 22 between the first and second pairs of planar side-walls, respectively. Optical paths 21 and 22 allow measurement of transmittance in two perpendicular directions, each optical path having a different length. Preferably, the length of the longer optical path is at least three times the length of the shorter optical path, thereby allowing measurement of optical transmittance in more than three orders of magnitude. First portion 11 may be made from any material suitable for optical analysis in the wavelengths of about 220 to about 380 nm or, preferably, in the wavelengths of about 220 to about 400 nm.

Figure 2A:
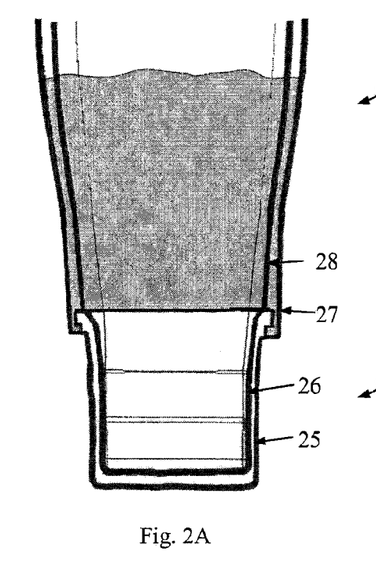
FIGS. 2A-2E: Fluid processing tubes according to the invention, the second portion being mechanically interlocked and/or fused to the first portion.
Figure 2B:
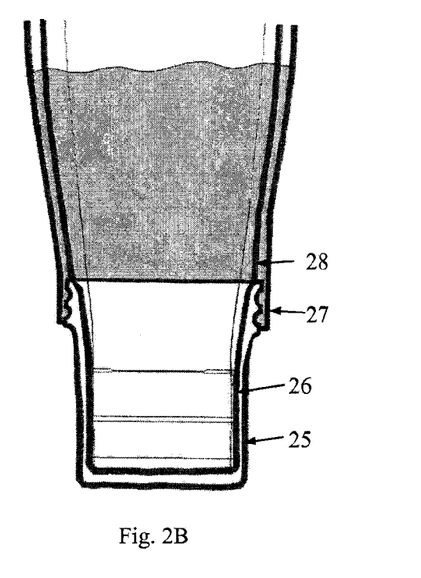
Figure 2C:
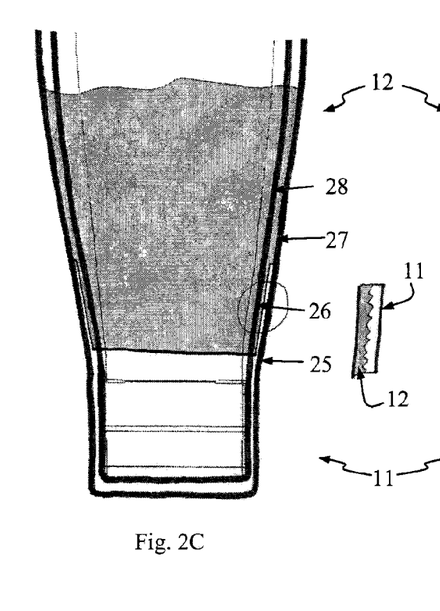
Figure 2D:
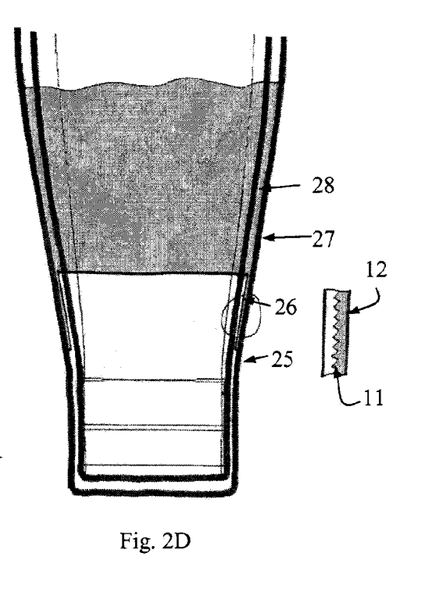
Figure 2E:
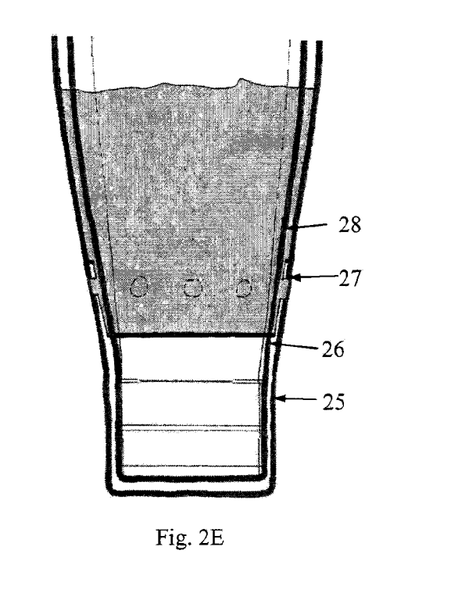

As FIG. 2A shows, the first and the second portion of tube 10 may also be mechanically interlocked by any combination of grooves and protrusions suitable therefore. Protrusions and grooves can be provided on outer walls 25, 27 and/or inner walls 26, 28 of first portion 11 and/or second portion 12. Some alternatives of interlocking first portion 11 and second portion 12 of tube 10 according to the present invention are shown in FIGS. 2A to 2E. Obviously, the skilled in the art will be able to conceive many similar ways of interlocking first portion 11 and second portion 12 of tube 10 and these embodiments shall also be encompassed by the present invention. As shown in FIG. 2A, the portions may additionally be welded to each other by frictional welding, ultrasonic welding, high frequency welding and/or bonding.

Figure 3A:
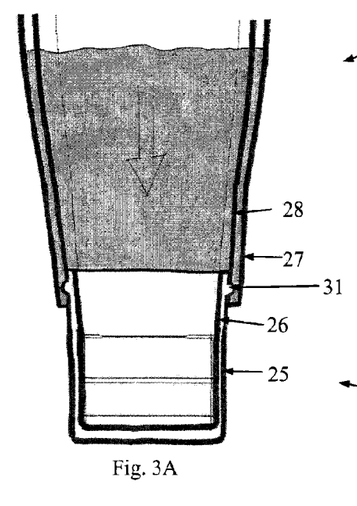
FIGS. 3A-3B: Fluid processing tubes according to the invention, the second portion being connected to the first portion by a snap connection.
Figure 3B:
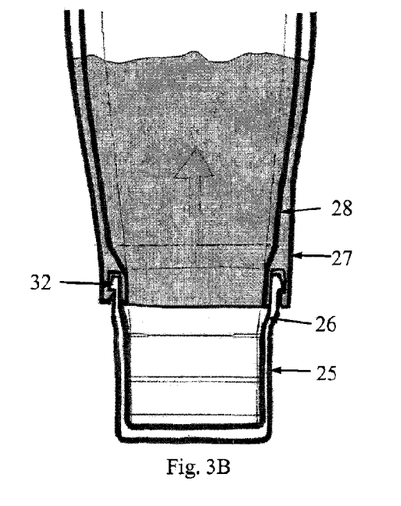

Furthermore, second portion 12 may be connected to first portion 11 by a snap-connection. Examples of snap-connections are releasable snap-connection 31 (FIG. 3A) and non-releasable snap-connection 32 (FIG. 3B).

Figures 4A, 4B:
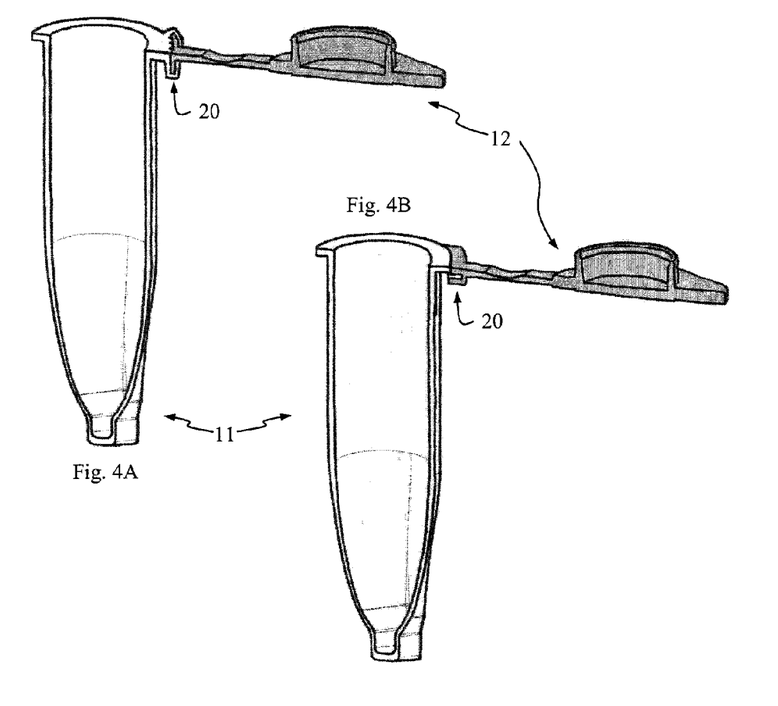
FIGS. 4A-4B: Fluid processing tubes according to the invention, the second portion being fused to the first portion near the joint between the fluid containing part of the tube and the cap.

When second portion 12 of tube 10 is connected to first portion 11 near joint 15 between fluid containing part 13 and cap 14, second portion 12 may be enclosed in rim 20 of fluid containing part 13 and fused or welded thereto (FIG. 4A). Alternatively, second portion 12 may cover rim 20 of fluid containing portion 13 and be fused or welded thereto (FIG. 4B).

Figure 5A:
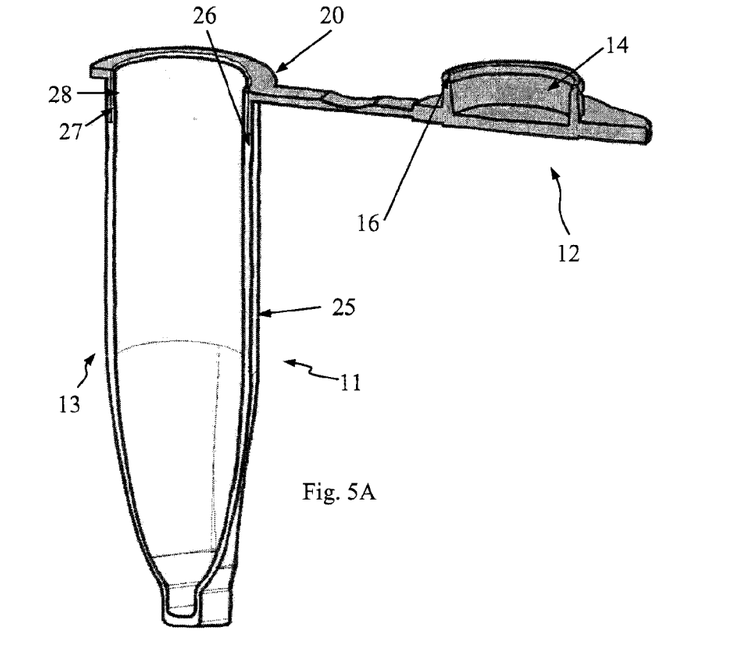
FIGS. 5A-5C: Fluid processing tubes according to the invention, the second portion being fused to the first portion in the uppermost section of the fluid containing part of the tube.
Figure 5B:
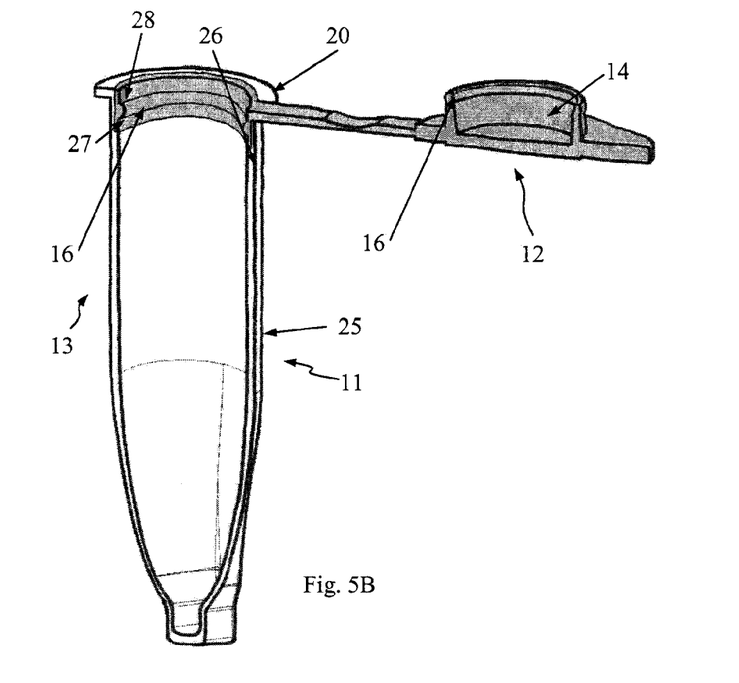
Figure 5C:
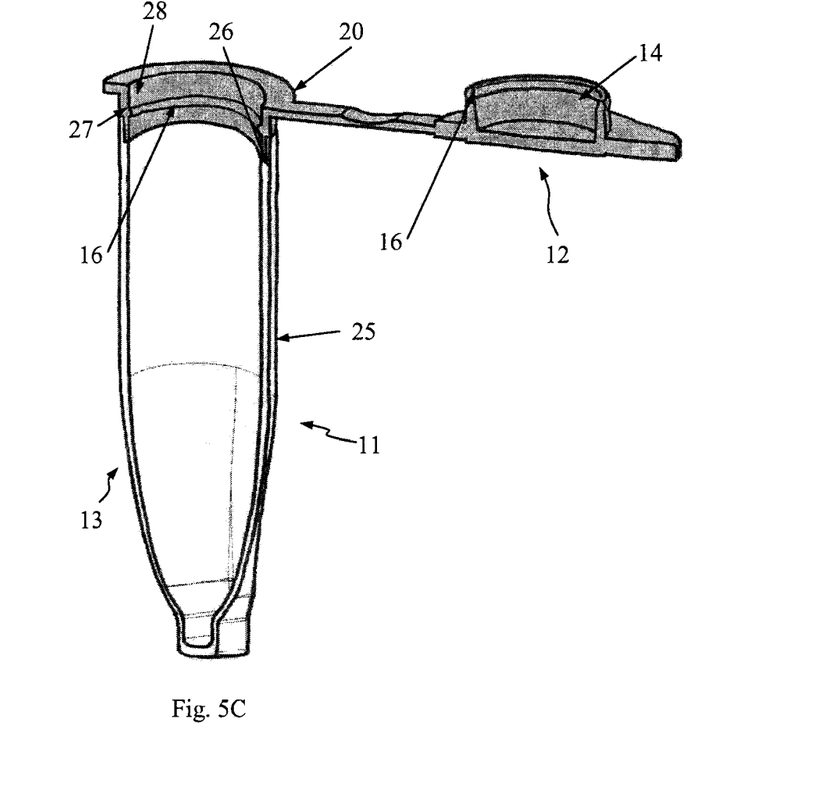

If second portion 12 is fused or welded to first portion 11 in the uppermost section of fluid containing part 13, inner wall 28 of second portion 12 may be welded to outer wall 25 of first portion 11 as shown in FIG. 5A. Alternatively, outer wall 27 of second portion 12 may be welded to inner wall 26 of first portion 11 or second portion 12 may be welded on top of first portion 11 as shown in FIG. 5B and FIG. 5C, respectively. As shown in these embodiments, rim 20 may be provided by first portion 11, second portion 12 or both. As also shown, cap closing means 16 for holding cap 14 on fluid containing pan 13 of tube 10 may be comprised so fluid containing part 13, cap 14, or both.

Figure 6A:
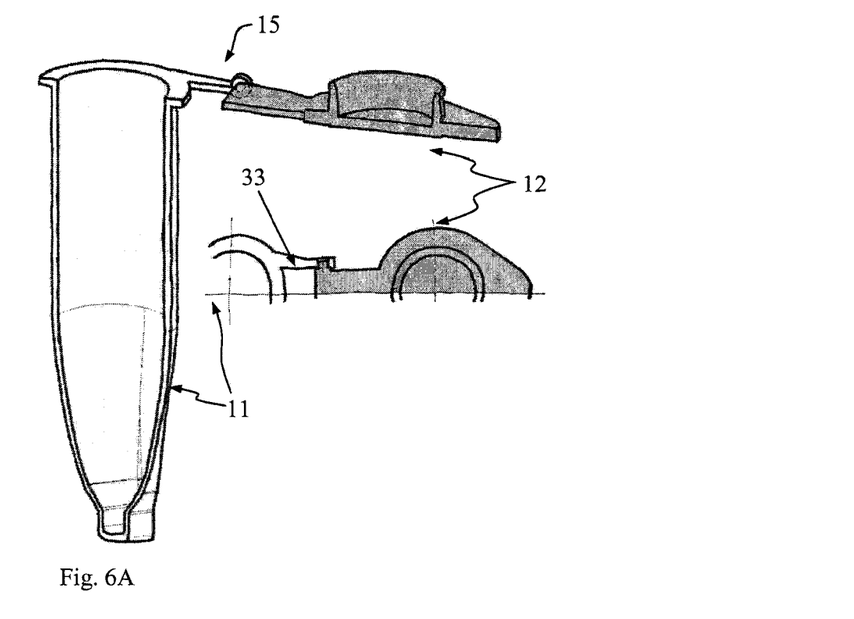
FIGS. 6A-6B: Fluid processing tubes according to the invention, the second portion being connected to the first portion at the joint between the fluid containing part of the tube and the cap by a joint created in in-mold assembly during injection molding.
Figure 6B:
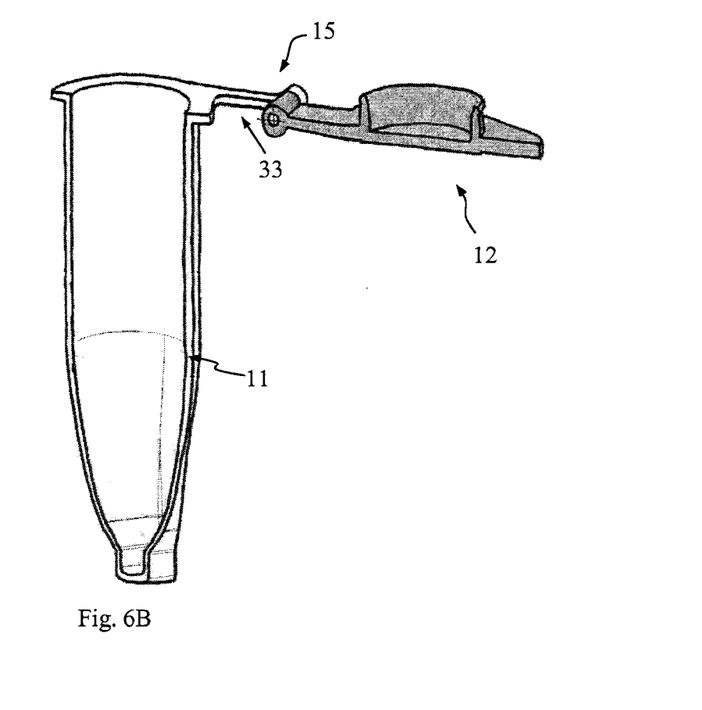
Figure 7A:
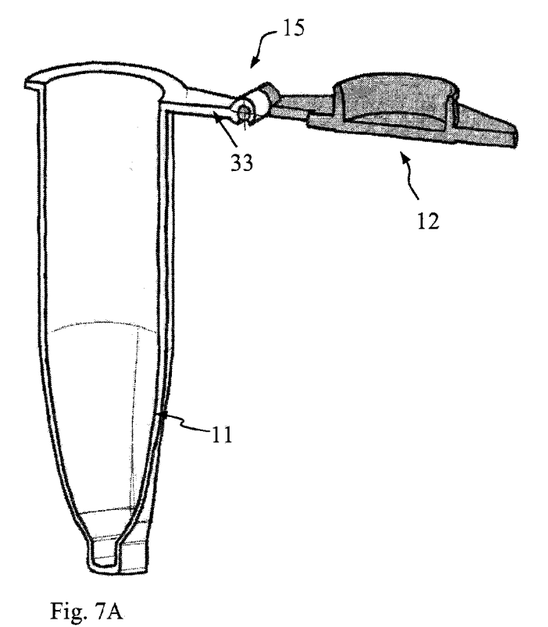
FIGS. 7A-7B: Fluid processing tubes according to the invention, the second portion being connected to the first portion at the joint between the fluid containing part of the tubs and the cap by a snap-joint.
Figure 7B:
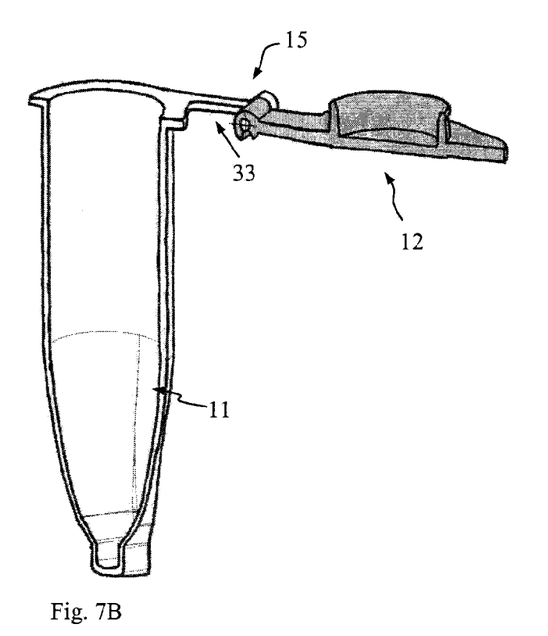

In further embodiments of the present invention, first portion 11 and second portion 12 are form-fitted at joint 15 between cap 14 and fluid containing pad 13 of tube 10. Form-fitted joints may be created in in-mold assembly during injection molding and as snap connections. For instance, FIG. 6A shows joint 15 created in in-mold assembly during injection molding wherein pin 33 is part of second portion 12 of tube 10. FIG. 6B discloses joint 15 created in in-mold assembly during injection molding wherein pin 33 is part of first portion 11 of tube 10. Similarly, when joint 15 is a snap connection, pin 33 may be part of second portion 12 (FIG. 7A) or first portion 11 (FIG. 7B) of tube 10.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the Figs. individually although they may not have bean described in the afore or following description. Also, alternatives of the embodiments described in the figures and the description and alternatives of features thereof can be disclaimed from the subject matter of the invention.

Furthermore, in the claims the word "comprising" does not exclude other elements or steps, and the indefinite article "a" or "an" does not exclude a plurality. A single unit may fulfill the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A fluid processing tube capable of being used in optical analysis, comprising:

a) a first portion being made from a first material suitable for optical analysis and being configured to include two optical paths of different lengths, and
b) a second portion connected to said first portion and being made from a second material different from said first material,
wherein said first portion comprises an optical detection zone,
wherein said optical detection zone has a rectangular cross-section when viewed in direction of a longitudinal axis of the tube and includes two optical paths of different lengths,
wherein the two optical paths are perpendicular to each other and perpendicular to the longitudinal axis of the tube,
wherein said first portion is configured to contain a fluid,
wherein said fluid processing tube is configured for centrifugation,
wherein said second portion is cylindrically shaped and has a tapered end which contains a combination of protrusions and grooves, and
wherein said first portion is mechanically interlocked to the tapered end of said second portion by the combination of protrusions and grooves.

2. The fluid processing tube according to claim 1, wherein the first portion is integral with the second portion.

3. The fluid processing tube according to claim 1, wherein the first portion and the second portion are welded, fused, bonded, form-fitted, frictional-fitted, or any combination thereof, to each other.

4. The fluid processing tube according to claim 1, wherein the first portion is connected to the second portion over at least one third portion.

5. The fluid processing tube according to claim 1, wherein said second portion comprises a cap.

6. The fluid processing tube according to claim 5, wherein said second portion further comprises a connector for connecting the cap to the fluid containing part of the tube over a joint.

7. The fluid processing tube according to claim 5, wherein said cap is connected to the fluid containing part of the tube over a joint.

8. The fluid processing tube according to claim 5, wherein said tube and/or said cap comprise at least one cap fixture for holding said cap when being closed.

9. The fluid processing tube according to claim 1, wherein said first material is suitable for optical analysis in the wavelengths of from 220 to 400 nm.

10. The fluid processing tube according to claim 9, wherein said first material is suitable for optical analysis in the wavelengths of from 220 to 380 nm.

11. The fluid processing tube according to claim 9, wherein said first material is suitable for optical analysis in the wavelengths of 230 nm, 260 nm, 280 nm, or any combination thereof.

12. The fluid processing tube according to claim 1, wherein said optical detection zone is positioned at an end of the tube which is opposite an opening thereof.

13. The fluid processing tube according to claim 1, wherein a side-wall of the optical detection zone comprises at least one planar area.

14. The fluid processing tube according to claim 1, wherein the length of the longest optical path is at least three times the length of the shortest optical path.

15. The tube according to claim 1, wherein said second material is softer and/or less brittle than said first material.

16. The tube according claim 1, wherein said first material is selected from the group consisting of cyclic olefin copolymers, cyclic olefin polymers, polymethylpenten, glass, graphene and PTFE, and wherein said second material is polypropylene or polyethylene.

17. The tube according to claim 1, wherein an inner volume of the optical detection zone is approximately 15 microliters or less.

18. A method for optically analyzing a fluid, comprising:
a) filling a liquid into a tube according to claim 1, and
b) optically analyzing said fluid in the tube.

19. A tube according to claim 1, capable of being used for processing, optically analysing, storing a fluid, or any combination thereof.

20. The fluid processing tube according to claim 1, wherein said first portion is distal to said second portion.

21. The fluid processing tube according to claim 1, wherein said first portion is distal to said second portion.

22. A fluid processing tube capable of being used in optical analysis, comprising:
a) a first portion suitable for optical analysis and being configured to contain a fluid, and
b) a second portion connected to said first portion being configured to include a cap for closing the first portion, wherein
c) the cap is connected to the first portion over a joint,
wherein said first portion comprises an optical detection zone,
wherein said first portion is configured to include two optical paths of different lengths,
wherein the two optical paths are perpendicular to each other and perpendicular to the longitudinal axis of the tube,
wherein said fluid processing tube is configured for centrifugation,
wherein said second portion is cylindrically shaped and has a tapered end which contains a combination of protrusions and grooves, and
wherein said first portion is mechanically interlocked to the tapered end of said second portion by the combination of protrusions and grooves.

23. The tube according to claim 22, wherein said first portion and said second portion comprise the same material.

24. The tube according to claim 22, wherein said first portion comprises a first material suitable for optical analysis and said second portion comprises a second material less brittle than said first material.

* * * * *